United States Patent [19]

Fukami et al.

[11] Patent Number: 4,489,603
[45] Date of Patent: Dec. 25, 1984

[54] MOISTURE SENSITIVE ELEMENT

[75] Inventors: Akira Fukami; Kunio Okamoto, both of Okazaki, Japan

[73] Assignee: Nippon Soken, Inc., Nishio, Japan

[21] Appl. No.: 415,546

[22] Filed: Sep. 7, 1982

[30] Foreign Application Priority Data

Sep. 9, 1981 [JP] Japan .................. 56-142007

[51] Int. Cl.$^3$ .................. G01N 19/10; G01N 27/12
[52] U.S. Cl. .................. 73/337; 200/61.06
[58] Field of Search .................. 73/335, 336, 336.5, 73/337, 338, 338.3, 73; 324/63, 65, 65 R; 338/35; 200/61.06; 236/44; 340/602, 604

[56] References Cited

U.S. PATENT DOCUMENTS 2,930,016  3/1960  Weston et al. .................. 73/336.5 X
3,540,278  11/1970  Diamond .................. 73/336.5

FOREIGN PATENT DOCUMENTS 0139651  8/1982  Japan .................. 73/335
0139652  8/1982  Japan .................. 73/335

Primary Examiner—John W. Caldwell, Sr.
Assistant Examiner—Vincent P. Kovalick
Attorney, Agent, or Firm—Cushman, Darby & Cushman

[57] ABSTRACT

A moisture sensitive element including a sheet made from a mixture of electrically insulating fibers having the property to expand upon adsorbing the moisture (e.g., cellulose fiber) and electroconductive fibers (e.g., activated carbon fiber). The moisture sensitive element is capable of sensing the humidity of the air by determining the electric resistance which varies according to the change of the humidity of the air, and can also be applied as a condensation sensor which can sense, for example, dew condensation on windowpanes.

17 Claims, 6 Drawing Figures

MOISTURE SENSITIVE ELEMENT

This invention relates to a humidity sensor capable of sensing the amount of water vapor in the air, that is, humidity of the air. More particularly, the invention relates to an electric resistance type humidity sensor, or a humidity sensor of the type in which the electric resistance varies according to the humidity of the air. The humidity sensor of this invention can be also applied as a condensation sensor which can sense, for example, dew condensation on windowpanes or such.

Many inventions and devices have been worked over this type of humidity sensor, and several models have been commercialized. A typical example of the commercialized products is a lithium chloride impregnated humidity sensor. This sensor is made by impregnating a natural cortex-made base sheet directly with a lithium chloride solution. This type of humidity sensor, however, has a disadvantage that the meansurable range of humidity is limited. Such sensor also has the problem that the deliquescent salt (lithium chloride) used therein is diluted in use with moisture in the air and drips down from the sensor body as liquid droplets, making the sensor unable to perform its normal function. Thus, this type of sensor is very short in its service life.

Another representative example of the commercialized humidity sensors is a magnesium-rutile system ceramic sensor. This humidity sensor comprises a porous sintered body made from $MgCr_2O_2$ and $TiO_2$, and it uses $RuO_2$ for electrode and is equipped with a heater for heat cleaning. While this type of humidity sensor has an advantage that it is capable of measuring humidity over a wide range, it has a drawback that it is incapable of long-time use unless the sintered body is heated and regenerated by the heater.

The above-mentioned two typical known humidity sensors also involve the following problems. This type of humidity sensors are based on the principle that the change of resistance caused by adsorption or desorption of moisture depends on the ionic conduction through moisture adsorption. Ordinarily, the resistivity of the device ranges from about 10 KΩ to about 10 MΩ, and for measurement of resistance, because of poor durability of the sensor, it is usual to apply an AC voltage of about 1 KHz and measure the AC resistance. However, in measurement of resistance, in general, the higher the resistivity, the greater difficulty is involved in the measuring circuit, and particularly the great difficulties are found in measuring a resistivity of over 100 KΩ. Further, for the measurement of AC resistance, provision of an AC power source is required, necessitating enlarged scale and high cost of the measuring apparatus.

Moreover, since said known types of sensors involve the technically difficult steps for the manufacture thereof, elevation of their manufacturing cost is inevitable.

As viewed above, the hitherto proposed humidity sensors had many problems such as poor durability, high cost and expensiveness of the measuring circuit used therefor.

The present invention has for its object to provide a humidity sensor which is easy and uncostly to manufacture and is also capable of high-performance measurement by use of a simple measuring circuit.

Figure 1:
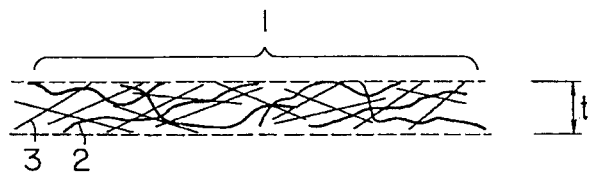
FIG. 1 is a schematic sectional view of an embodiment of the present invention.

In the drawings, reference numeral 1 designates humidity sensor, 2 cellulose fibers, 3 carbon fibers, 11 and 12 holding members serving as insulators, 13 electrodes, and 14 clips.

The present invention is described in detail hereinbelow by way of the embodiments thereof as illustrated in the drawings.

Referring to FIG. 1, there is shown a schematic sectional view on an enlarged scale for illustrating an embodiment of the invention. In the drawing, numeral 1 indicates generally a humidity sensor, 2 the cellulose fibers, and 3 the carbon fibers. The broken lines in the drawing indicate the surfaces of the humidity sensor 1.

The humidity sensor 1 is a paper-like assembly of said fibers. Cellulose fiber 2 is one which is same as or equivalent to that usually used as paper material. Used as carbon fiber 3 in this embodiment is one having a diameter of 3-20 μm and a length of about 1-5 mm. This humidity sensor 1 was given a thickness of about 0.1-0.4 mm. As for the size (area) of the humidity sensor 1, although it is possible with this invention to make a sensor of any desired area ranging from about 5 mm square to about 100 mm square, there were produced in this embodiment the sample sensors having an area of about 10-30 mm square.

The production method of the humidity sensor 1 is completely same as the paper-making process commonly used for making Japanese paper from cellulose fiber. That is, the humidity sensor according to this invention can be manufactured very easily by simply mixing suitable amounts of cut pieces of cellulose fiber 2 and carbon fiber 3 and subjecting the mixture to said paper-making process. In this case, a large-sized sheet (such as 1 m square) may be made and this sheet may be suitably cut to form the humidity sensors 1 of a desired size.

Figure 2:
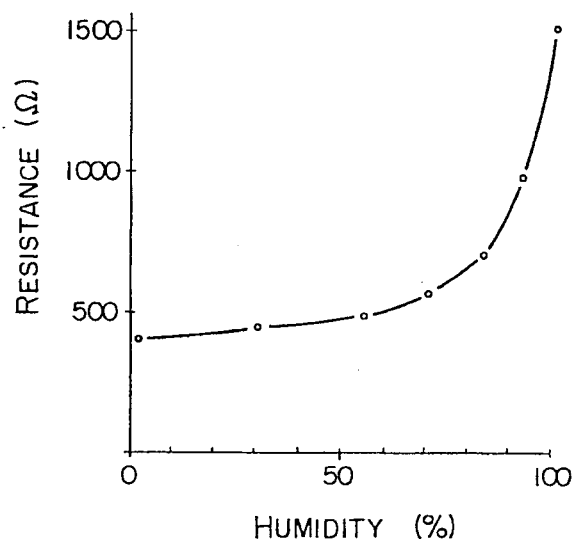
FIG. 2 is a humidity-resistance characteristic diagram showing the characteristic properties of the humidity sensor according to this invention.

Now, the operation of the humidity sensor according to this invention is described. Referring to FIG. 2, there is shown a humidity-resistance characteristic curve as determined from the embodiment shown in FIG. 1. The "resistance" referred to herein means the resistivity across both ends of the humidity sensor 1. It will be seen that the resistivity increases as the humidity rises up, with such tendency becoming conspicuous when the humidity is over 70%. Also, from the fact that the maximum resistivity of the sensor of this invention is around 1 kΩ, which is far lower than those of the conventional humidity sensors, it will be understood that the operation for measuring the resistivity of the humidity sensor of this invention as well as the measuring circuit used therefor may be simple as compared with the conventional devices.

The operational characteristic as represented by FIG. 2 of the humidity sensor 1 according to this invention may be accounted for as follows. Cellulose fiber 2 may be regarded as an insulator. Carbon fiber 3, through a conductor, has a slight resistance. A great many of carbon fibers 3 lie in succession while entangled with each other across both ends of the sensor 1. Therefore, there exists contact resistance between every two adjoining carbon fibers. Accordingly, the resistance across both ends of the humidity sensor 1 is the sum of resistance of the carbon fiber itself and contact resistance. More definitely, the total resistivity is decided by calculating comprehensively the resistances created by the carbon fibers contacting each other in both serial and parallel arrangements. Thus, the resistivity of the humidity sensor 1 of this invention is different from those of the conventional sensors ultilizing ionic conduction, and it is therefore possible with the sensor of this invention to easily obtain a very low resistivity.

The humidity sensor 1, when exposed to moisture, operates as described below. It is well known that cellulose fiber or paper made from cellulose fiber adsorbs moisture in the air. It is also known that the moisture pickup depends on humidity of the air and increases proportionally as the humidity rises. It is further known that the moisture-adsorbed cellulose fiber expands 20 to 30% as much as the original size. Now, when the humidity sensor of this invention is exposed to moisture, the cellulose fibers 2 adsorb moisture in the air and are thereby expanded. As the cellulose fibers are thus expanded and enlarged in volume, the carbon fibers which have been in contact with each other are forced to disjoin from each other at many parts. Consequently, the number of the carbon fibers joined at both ends of the humidity sensor 1 is decreased, causing a corresponding increase of resistivity. The increase of resistivity depends on the degree of expansion of the cellulose fibers which, in its turn, depends on the humidity in the air. Thus, the resistivity of the humidity sensor 1 is decided straightforwardly by the humidity of the air.

When the humidity changes from high to low, moisture drifts away from the cellulose fibers to cause contraction thereof, with the result that the carbon fibers restore their original state of contact to lower the resistivity to its original level.

Here, the cellulose fiber and carbon fiber mixing ratio is discussed. A too low content of cellulose fibers leads to a poor strength of the humidity sensor 1 which is a paper-like product, so that it is desirable that the mixing ratio of cellulose fiber is not less than 30% of the whole fiber mixture. On the other hand, a too low content of carbon fibers invites an increase of resistance of the humidity sensor 1, so that the carbon fiber mixing ratio should not be less than 10% of the whole fiber mixture. By taking into account the abovesaid relation between cellulose and carbon fibers in the fiber mixture, the mixing ratio of each fiber is suitably selected such that a desired resistivity will be provided with a predetermined size of the humidity sensor.

Figure 3:
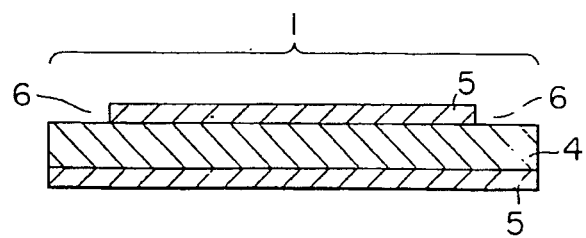
FIG. 3 is a schematic sectional view of another embodiment of this invention.

Referring now to FIG. 3, there is shown a schematic sectional view of a second embodiment of this invention. In the drawing, numeral 4 indicates the portion made from a mixture of cellulose fibers and carbon fibers, 5 the portions made from the cellulose fibers alone, and 6 the electrode portions. Sensing of humidity is performed in the mixed fiber portion 4 in the same way as in the first embodiment described above. The portions 5, being made from cellulose fibers along and hence having high strength, serve as a reinforcement of the humidity sensor 1. Said portions 5 preferably have a thickness of about 0.05–0.1 mm. This is because a smaller thickness can not conduce to enhancement of strength while a greater thickness requires much time for moisture in the air to reach the mixed fiber portion 4, resulting in poor responsiveness to humidity to be sensed. The portion 5 on one side is cut out at its both ends to provide the electrode portions 6. Such cutouts are required for measuring the resistance in the portion 4 since the portions 5 made from cellulose fibers alone are an insulator. In the embodiment shown in FIG. 3, said portions 5 are provided on both sides of the sensor body, but such portion 5 may be provided on one side alone if no problem of strength is involved.

Figure 4:
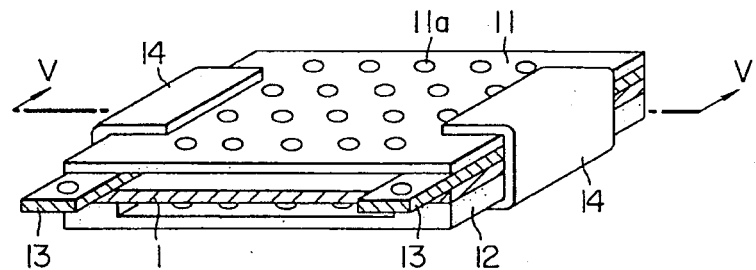
FIG. 4 is a schematic perspective view showing still another embodiment of this invention.
Figure 5:
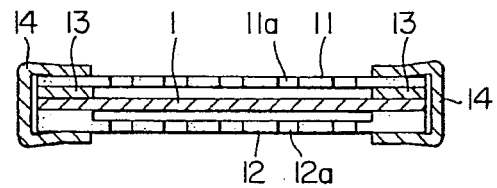
FIG. 5 is a sectional view taken along the line A—A of FIG. 4.

Being a paper-like product, the humidity sensor 1 described above is subject to a certain limitation in strength and it may break when an extraneous object touches it. The embodiment shown in FIGS. 4 and 5 is designed to do away with such problem. In this embodiment, there are provided the holding members 11, 12 adapted to protect the humidity sensor 1 against breakage from external factors and also serving to retain the shape of the sensor. Said holding members 11, 12 are formed with a plurality of pores 11a, 12a for assuring passage of air to the humidity sensor 1. Also, said members 11, 12 should be insulating to such an extent as will not obstruct any change of resistance that occurs in the humidity sensor 1. Since these holding members need to have rigidity, bakelite was used for said members in this embodiment. Clips 14 are adapted to clamp together the humidity sensor 1, electrodes 13 and holding members 11, 12 into an integral assembly. In this embodiment, spring steel is used for said clips for pressing down said elements by spring force, but screws may be employed instead of such clips.

Figure 6:
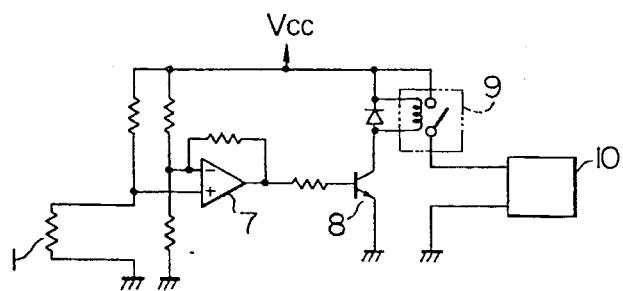
FIG. 6 is an electric circuit diagram incorporating the humidity sensor of this invention.

FIG. 6 shows a circuit diagram exemplifying the practical adaptation of the humidity sensor according to this invention illustrated in FIGS. 1 and 3-5. In FIG. 6, reference numeral 7 denotes a comparator, 8 a transistor, 9 a solenoid relay, and 10 a dehumidifier. The operation of this system is roughly as follows. When the humidity of the ambient air increases to cause a corresponding rise of resistance of the humidity sensor 1, the input voltage to the comparator 7 increases, and when such input voltage rises above the standard voltage which has been previously set according to the standard resistance, the comparator 7 outputs "1" to make the transistor 8 conductive, whereby the relay 9 also becomes conductive to operate the dehumidifier 10.

As described above, the humidity sensor of this invention, unlike the conventional sensors utilizing ionic conduction, is low in resistivity and also allows measurements by way of DC resistance, so that in use of the humidity sensor of this invention it is possible to accomplish desired measurement or control with a very simple circuit such as shown in FIG. 6.

Further, the humidity sensor 1 of this invention is capable of sensing humidity over a wide range as illustrated in FIG. 2 and also finds use as a condensation sensor. This owes to the fact that the cellulose fiber has as well water-adsorbing capacity as its hygroscopic capacity and also shows the same expansion characteristic as in the case of a humidity sensor. Therefore, it goes without saying that the device of this invention can be also used as a water sensor (a sensor for detecting presence or absence of water).

In the foregoing embodiments of the invention, cellulose fiber and carbon fiber are used as composing materials of the humidity sensor 1, but it is possible to replace cellulose fiber with polyvinyl alcohol fiber or a mixture of cellulose fiber and polyvinyl alcohol fiber. In other words, it is possible to use any of these fibers which have a capacity to adsorb moisture according to humidity of the air (most of the fibrous materials have such hygroscopicity) and also have a nature to expand by itself upon adsorption of moisture, or a combination or mixture of these fibers. Also, carbon fiber may be replaced with activated carbon fiber. Thus, it is possible in this invention to use any of the conductive fibers. However, metallic fibers (such as stainless fiber) are unfavorable because use of such metallic fibers makes the paper making process difficult to carry out because of their rigidity. No matter what type of fiber is used for each fiber component, the fiber mixing ratio is same as said above.

Further, bakelite used for the holding members 11, 12 in the foregoing embodiments may be replaced with porous ceramic material. In the latter case, electrodes 13 may be formed by coating the surface of said porous ceramic material with a metallic material.

As described above, the humidity sensor according to this invention is composed of a sheet made from a mixture of a hygroscopic and expandable fiber such as cellulose fiber and a conductive fiber such as carbon fiber, so that such humidity sensor is low in manufacturing cost and also a simple measuring circuit can be used for the operation of the sensor.

Further, the humidity sensor of this invention is proof against damage from extraneous factors as the sensor body is protected by the air-permeable and rigid plate-like insulators.

What is claimed is:

1. A moisture sensitive element, comprising:
   a sheet made from a mixture of electrically insulating fibers having a property of expanding upon absorbing moisture and electroconductive fibers having a length of 1–5 mm, the ratio of the electrically insulating fibers being 30% or more of the total fiber mixture in the sheet, and the ratio of the electroconductive fibers being 10% or more of the total fiber mixture in the sheet.

2. The moisture sensitive element according to claim 1, wherein:
   the electrically insulating fibers having a property of expanding upon absorbing moisture are cellulose fibers.

3. The moisture sensitive element according to claim 1, wherein:
   the electrically insulating fibers having a property of expanding upon absorbing moisture are a mixture of cellulose fibers with polyvinyl alcohol (PVA) fibers.

4. The moisture sensitive element according to claim 1, wherein:
   the electroconductive fibers are carbon fibers.

5. The moisture sensitive element according to claim 1, wherein:
   the electroconductive fibers are activated carbon fibers.

6. The moisture sensitive element according to claim 3, wherein:
   the electrically insulating fibers having a property of expanding upon absorbing moisture are a mixture of cellulose fibers with PVA fibers, and the electroconductive fibers are activated carbon fibers.

7. The moisture sensitive element according to any one of claims 1–6, wherein:
   at least one side of said sheet is covered with a layer not containing the electroconductive fibers.

8. A moisture sensitive element, comprising:
   a sensor unit composed of a sheet made from a mixture of electrically insulating fibers having a property of expanding upon absorbing moisture and electroconductive fibers having a length of 1–5 mm, the ratio of the electrically insulating fibers being 30% or more of the total fiber mixture in the sheet, and the ratio of the electroconductive fibers being 10% or more of the total fiber mixture in the sheet, said unit being held on its both sides by air-permeable and rigid plate-like insulators;
   a pair of electrodes disposed between said sensor unit and said insulators; and
   securing members for securing said sensor unit, insulators and electrodes as an integral assembly.

9. The moisture sensitive element according to claim 8, wherein:
   the electrically insulating fibers having a property of expanding upon absorbing moisture are cellulose fibers and polyvinyl alcohol fibers, and the electroconductive fibers are carbon fibers and activated carbon fibers.

10. The moisture sensitive element according to claim 8 or 9, wherein:
    the air-permeable and rigid plate-like insulators are comprised of plate-like ceramic material.

11. A moisture sensing unit, said unit comprising:
    a moisture sensitive element according to any one of claims 8–13, said element being held on its both sides by air-permeable and rigid plate-like insulators;
    a pair of electrodes disposed between said sensitive element and said insulators; and
    securing members for securing said sensitive element insulators and electrodes as an integral assembly.

12. The moisture sensitive element according to claim 8, wherein:
    the electrically insulating fibers having a property of expanding upon absorbing moisture are cellulose fibers, and the electroconductive fibers are carbon fibers.

13. The moisture sensitive element according to claim 8, wherein:
    the electrically insulating fibers having a property of expanding upon absorbing moisture are cellulose fibers, and the electroconductive fibers are activated carbon fibers.

14. The moisture sensitive element according to claim 8, wherein:
    the electrically insulating fibers having a property of expanding upon absorbing moisture are cellulose fibers, and the electroconductive fibers are carbon fibers and activated carbon fibers.

15. The moisture sensitive element according to claim 8, wherein:
    the electrically insulating fibers having a property of expanding upon absorbing moisture are polyvinyl alcohol fibers, and the electroconductive fibers are carbon fibers.

16. The moisture sensitive element according to claim 8, wherein:

the electrically insulating fibers having a property of expanding upon absorbing moisture are polyvinyl alcohol fibers, and the electroconductive fibers are activated carbon fibers.

17. The moisture sensitive element according to claim 8, wherein:
the electrically insulating fibers having a property of expanding upon absorbing moisture are polyvinyl alcohol fibers, and the electroconductive fibers are carbon fibers and activated carbon fibers.

* * * * *